United States Patent [19]

Schoenwald et al.

[11] Patent Number: 4,975,449
[45] Date of Patent: Dec. 4, 1990

[54] TOPICAL TREATMENT OF GLAUCOMA WITH 2-BENZOTHIAZOLESULFONAMIDE DERIVATIVE

[75] Inventors: Ronald D. Schoenwald; Charles F. Barfknecht, both of Iowa City, Iowa

[73] Assignee: University of Iowa Research Foundation, Iowa City, Iowa

[21] Appl. No.: 464,063

[22] Filed: Feb. 4, 1983

[51] Int. Cl.$^5$ ............................................. A61K 31/425
[52] U.S. Cl. ..................................... 514/367; 514/913
[58] Field of Search ................. 424/270; 514/367, 913

[56] References Cited

U.S. PATENT DOCUMENTS 4,386,098  5/1983  Woltersdorf et al. .............. 424/270

FOREIGN PATENT DOCUMENTS 0036351  9/1981  European Pat. Off. .
795174  5/1958  United Kingdom .

OTHER PUBLICATIONS

Am. J. Vet. Res. 40(3), 334–345 (1979)—Gelatt et al.
AMA Drug Evaluation, 2nd ed.—1973—pp. 676; 678–679, 684–685–Publishing Science Group, Inc., Acton, Mass.
Investigative Ophthalmology 13(7), 479–483–Maren.
Drug Res. 25(5), 806–808 (1975)—de Feo et al.

Primary Examiner—Douglas W. Robinson
Attorney, Agent, or Firm—Zarley, McKee, Thomte, Voorhees & Sease

[57] ABSTRACT

A topical composition for eye treatment of glaucoma, comprising a small but pharmaceutically effective amount of an analog of benzothiazole-2-sulfonamide. The most preferred compound is 6-chloro-benzothiazole-2-sulfonamide. The invention also relates to a method of topically treating glaucoma with eye drops to reduce intraocular pressure. Finally, disclosed is a method of synthesis of the preferred and highly effective benzothiazole-2-sulfonamide analogs, particularly the 6-chloro-benzothiazole-2-sulfonamide compound.

17 Claims, No Drawings

TOPICAL TREATMENT OF GLAUCOMA WITH 2-BENZOTHIAZOLESULFONAMIDE DERIVATIVE

GRANT REFERENCE

This invention was made with Government support under Contract No. 5 RO1 EY 03297-02 awarded by the National Eye Institute. The Government has certain rights in this invention.

BACKGROUND OF THE INVENTION

Glaucoma, which some estimate affects 2 million adults over 40, is an impairment of vision caused by too much fluid pressure within the eye.

Surgical treatment for glaucoma is effective, however, it is expensive and some surgeons will use surgery only as a last resort.

Carbonic anhydrase inhibitors, prescribed orally work well to treat this disease, but they carry a host of side effects, from nausea to kidney stones.

Glaucoma stems from an excess of fluid behind the cornea, the three-layered tissue that acts as a window to let light enter. Fluid carrying nutrients such as potassium and glucose constantly wash the inside of the cornea to keep it healthy, much as tears wash the outside of the cornea.

In some middle-aged adults fluids build up faster than can be absorbed back into the blood, for one of two reasons: the ciliary body (a tiny tissue behind the iris) may excrete too much fluid, or the fluid may not drain off at the normal rate.

Either way, the excess fluid damages the optic nerve. At first a glaucoma victim usually experiences a subtle loss of peripheral vision—objects will seem to disappear from certain spots to the side. But glaucoma often leads to middle-age blindness.

Unfortunately, the two approaches to general drug usage in treating glaucoma—topical (dropped into the eye) and oral—each have a peculiar set of side effects.

To make the long journey, oral drugs must be dosed in very high concentration. One class of drugs, called carbonic anhydrase inhibitors, slow the formation of fluid by inhibiting a chemical reaction at the ciliary body. Along with their well-tested effectiveness, comes nausea, tingling in fingers and toes and other side effects. Oral drugs generally do not, however, cause side effects in the eye.

Certain topical drugs, while causing less systemic effects, on the other hand, can cause severe headaches and constrict the pupil, making the daytime appear dark.

Accordingly, there is a real and continuing need to develop an inhibitor drug that can be dropped into the eye instead of swallowed, thereby avoiding the present side effects. It is a primary objective of the present invention to develop a highly effective topical carbonic anhydrase inhibitor drug (which previously is only effective orally) for treatment of glaucoma to reduce intraocular eye pressure, and at the same time, avoid the systemic side effects, commonly caused by oral drugs.

Another objective of the present invention is to develop a drug for topical treatment of glaucoma, which is not only effective, but which will also pass through the three layered cornea and still be effective enough to work on the ciliary body.

Another objective of the present invention is to develop a highly effective, topical drug treatment for glaucoma which is substantially non-harmful to the eye when topically applied.

An even further objective of the present invention is to develop an eye treating topical composition which is effective for glaucoma treatment.

A still further objective is to provide a convenient method of synthesis of certain new and novel compounds which are highly effective topical treatments for glaucoma.

A further specific objective of the present invention is to provide as a novel compound, 6-chloro-benzothiazole-2-sulfonamide, which in pharmaceutically effective amounts is a highly effective topical composition for eye drop treatment of glaucoma.

The method and manner of achieving each of the above objectives, as well as others, will become apparent from the detailed description of the invention which follows hereinafter.

SUMMARY OF THE INVENTION

A topical composition for eye drop treatment of glaucoma which comprises a small but pharmaceutically effective amount of an analog of benzothiazole-2-sulfonamide of the formula:

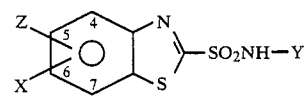

with the constituents as hereinafter defined.

The invention also relates to the most highly preferred compound 6-chloro-benzothiazole-2-sulfonamide, which is a compound falling into the general formula presented above. The invention further relates to a method of topically treating glaucoma with eye drops to reduce intraocular eye pressure; and finally, the invention relates to a method of synthesis of analogs of benzothiazole-2-sulfonamide.

DETAILED DESCRIPTION OF THE INVENTION

As heretofore mentioned, carbonic anhydrase inhibitors are known. However, the compounds are generally not effective because of the rather severe side effects previously mentioned. Studies have shown that when taken orally, because of the side effects, approximately 80% of the treated patients stop taking the drug treatment within two to three weeks. The side effects that they often report are short-term tingling of the extremities, gastrointestinal tract upset, kidney stones and some renal failure.

The mechanism of reaction of carbonic ahydrase inhibitors has been reported, and it is a combination of a diuretic effect and reduction of intraocular pressure in the eye. The compounds useful for treatment in this invention function to provide reduction of intraocular pressure, but do so without the commonly occurring side effects of oral drugs for treating glaucoma, or the commonly occurring side effects of topical drugs for glaucoma treatment.

The compounds developed by the applicants and useful for the topical composition eye drop treatment of glaucoma, as described in this invention, are analogs of benzothiazole-2-sulfonamide, and are carbonic anhydrase inhibitors. They have the following general formula:

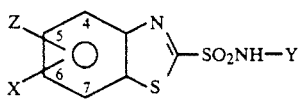

wherein "X" is a 4, 5, 6 or 7 positioned substituent, and "Z" is positioned on any of the other 4, 5, 6, or 7 positions, after "X" is selected, and wherein both "X" and "Z" are selected from the group consisting of hydrogen, halogens, methoxy, hydroxy, $C_1$ to $C_6$ hydroxyalkoxy, amino, amide, nitro, and trifluoromethylsulfonyl, and wherein if either "X" or "Z" is hydrogen, the other is not hydrogen; and Y is selected from the group of hydrogen and $C_1$ to $C_6$ alkyl.

Of course, the compound is carried in an inert, non-eye irritating, non-toxic eye drop diluent of conventional formulation. Such formulations are well known, and commonly referred to in, for example, the *Physician's Desk Reference for Ophthalmology* (1982 Edition, published by Medical Economics Company, Inc.,Oridell, New Jersey), wherein numerous sterile ophthalmologic ocular solutions are reported, e.g., see pp. 112–114, which are incorporated by reference.

Preferably the amount of the benzothiazole-2-sulfonamide analog present in the eye drop treatment composition is a concentration of from about 0.25% to about 5% by weight of the eye drop treating composition. Most preferably, the amount is from about 0.5% to about 2.0% by weight of the eye drop treating composition, and in tests conducted to date, highly effective compositions have used the compounds at the 1% suspension level.

As heretofore mentioned, while the diluent is not part of the present invention in that such diluents are known, it is preferred that the diluent be an isotonic eye treatment carrier, buffered to a pH within the range of from about 4.0 to about 8.0 and containing a small but effective amount of a wetting agent and an anti-bacterial agent. The preferred pH range is from about 6.8 to about 7.8.

Commonly used wetting agents are well known, and again are mentioned in the previously referred to pages of the *Physician's Desk Reference for Ophthalmology*. One suitable one is Tween, and in particular, Tween 80. Likewise, anti-bacterials are known and commonly employed in such compositions. Suitable anti-bacterials include the most preferred benzalkonium chloride and others as well such as, for example, chlorobutanol. The amount of wetting agent can range from 0.01% to 0.10%.

The amount of anti-bacterial can range from about 0.004% to about 0.02% by weight of the eye drop treating composition.

The compounds of this invention, providing that the molecular structures are as defined hereinbefore, are water soluble, but they also have a lipid solubility factor to allow transfer across the eye, and they have suitable structure to allow them to effectively function in the eye as carbonic anhydrase inhibitors. Their water solubility means ease of preparation for topical application, their lipid solubility characteristics mean effectiveness in transfer across the three corneal layers.

The compounds which are most preferred, because their effectiveness has been so far demonstrated to be the best, are 6-halobenzothiazole-2-sulfonamides, wherein "Z" and "Y" are hydrogen and "X" is a 6 position substituent. The preferred compounds are chloro, fluoro and bromo substituents for the "X" positioned moiety, with the 6-chloro being the most highly preferred.

As will be explained hereinafter, the dosage amounts can vary, and no doubt will vary, but are well within routine experimentation of the treating physician. In the test described hereinafter, the dosage for the topical application has been three drops, with one drop every two minutes. This has been found to be effective, but it is also reasonable to expect that other dosage levels will vary depending upon severity of the case.

It is believed that the present topical application constitutes the first ever topical application for reduction of intraocular pressure by carbonic anhydrase inhibition for glaucoma treatment, which is both at a practical dosage and which does not cause side effects at a sufficient magnitude to discourage the patient from continued use.

A certain few of the compounds, per se as described by the generic formula as presented previously, are known. However, none of those have ever been known to have the utility of effective topical treatments for glaucoma. The compounds that the applicant knows as previously reported are described in Korman, *Journal of Organic Chemistry* (1958), 23, 1768. Those compounds show the following: A four position methyl; a 6 position methyl; a 5 position chloro; a 4 position methoxy and a 6 position methoxy. In addition, the 6 ethoxy compound is known, see Topliss, "Diuretics" in Ch. 38, "Medicinal Chemistry, ed. A. Burger, 3rd ed., Part II, Wiley, Interscience, New York 1960, p. 985, and finally, benzothiazole-2-sulfonamide (X=Y=H) is known. Miller, et al., *Heterocyclic Sulfonamides, as Carbonic Anhydrase Inhibitors*, Journal of the American Chemical Society, Vol. 72 (1950), pp. 4893–4896. In each instance, above described, everything else not referred to at one of the specific positions in the basic ring structure earlier shown, is hydrogen. Other compounds, however, which have been synthesized are believed to be novel compounds. In particular, the following compounds are some of those that have been synthesized and are believed novel:

N-methyl-2-benzothiazolesulfonamide,
N-acetyl-2-benzothiazole-sulfonamide,
N-acetyl-6-ethoxy-2-benzothiazolesulfonamide,
6-ethoxy-N-methyl-2-benzothiazolesulfonamide,
6-ethoxy-N-propyl-2-benzothiazolesulfonamide,
6-hydroxy-N-methyl-2-benzothiazolesulfonamide,
6-hydroxy-2-benzothiazole-sulfonamide,
6-chloro-2-benzothiazolesulfonamide,
6-0-acetyl-2-acetyl-2-benzothiazolesulfonamide,
6-hydroxyethoxybenzothiazolesulfonamide,
6-benzyloxybenzothiazole-2-sulfonamide,
7-chloro-2-benzothiazolesulfonamide,
6 amino-benzothiazolesulfonamide,
6-fluoro-2-benzothiazolesulfonamide,
6-bromo-2-benzothiazolesulfonamide,
and 4, 6-dichloro-2-benzothiazolesulfonamide.

It should be understood that the applicants are not stating definitely that each of these are superior for the treatment of the present invention. Before arriving at such conclusions, detailed rabbit study testing will have to be made. However, it is reasonably predictable that all of these compounds will be operable to some extent, particularly in multiple dosage over long term. This conclusion is buttressed by the fact that those which have been subjected to intraocular testing in rabbit eyes, as indicated in the examples below, show significant effect, upon single dosage.

In accordance with the synthesis technique of this invention, it has been found that the analogs of benzothiazole-2-sulfonamide can be conveniently synthesized in a relatively simple and straightforward reaction, and at high yield. In particular, para-chloroaniline is reacted with sulfur chloride in typical Herz reaction to provide 2-mercapto-4-chloroaniline. The Herz reaction is known and is reported at Warbarton, W.K., Chem. Rev. 57, 1011 (1957) which is incorporated herein by reference. The next step is reaction with carbon disulfide to provide 2-mercapto-6-chlorobenzothiazole.

The 2-mercapto-6-chloro-benzothiazole formed in this reaction step is the immediate precursor of the topically effective carbonic anhydrase inhibitor, which is the most highly preferred, 6-chloro-benzothiazole-2-sulfonamide. In the next step, this compound is converted to a corresponding sulfenamide. Thereafter, the sulfenamide is oxidized to a sulfonamide to produce the desired benzothiazole-2-sulfonamide. The details of the steps of the synthesis will become apparent from the detailed description of such shown in the examples It should be mentioned that the phrase "Herz reaction" as used herein is intended to mean the introduction of a mercapto group ortho to an amino group. This is the commonly accepted and understood definition of a Herz reaction.

The following examples are offered to further illustrate the synthesis of the compounds of this invention, the making of topical treatment compositions using the same, and to provide data showing decrease of intraocular pressure in the cornea of rabbits. They are intended to further illustrate, but not necessarily limit the invention and it is understood that certain modifications and changes, both in technique and composition and structure, may be made, without departing from structure, function and operation of the invention

EXAMPLES

EXAMPLE 1

Synthesis of N-Methyl-2-benzothiazolesulfonamide

A solution of 40% aqueous methylamine (100 ml) was placed in a 250 ml 3-neched flask, equipped with a powerful stirrer and 2-addition funnels The solution was cooled to $-10°$ C. with an ice/methanol bath. A solution of 2-mercapto-benzothiazole (2.0g; .012 mol) in 30 ml of 5% NaOH was prepared, cooled to 10° C. and placed into one of the addition flasks. The second addition flask was charged with 50 ml of 5.25% $NaOC_1$ which was cooled to 5° C. The two solutions were added simultaneously to the aqueous methylamine over a period of one hour with the rate of addition of the 2-mercaptobenzothiazole solution slightly faster than the addition of the $NaOC_1$ solution. The temperature of the reaction was kept below 0° C. The reaction was stirred for 30 minutes upon completion of the addition. The reaction was removed from the ice bath and stirred for 30 minutes at room temperature. The N-methyl-2-benzothiazolesulfenamide was an oily substance at room temperature. The sulfenamide was extracted from the aqueous layer using ether ($2 \times 100$ ml) and the ether layer was washed with 50 ml of water. The ether layer was dried over $Na_2SO_4$ and the ether removed in vacuo. The green/blue oil was immediately dissolved in acetone (100 ml) and oxidized with 5% $KMnO_4$ (60 mol). The temperature of the oxidation was kept below 30° C. The $MnO_2$ was removed by vacuum filtration and the filter cake washed with 25 ml of 5% NaOH. The acetone was removed in vacuo and the N-methyl-2-benzothiazolesulfonamide precipitated upon acidification with 5% $HC_1$. The product was filtered and dried (42.8% yield). The product was purified by dissolving it in 10% $Na_2CO_3$ and precipitating it with 5% $HC_1$. m.p. 151° C.-153° C.; NMR(DMSO-D $/D_2O$) $8.5=7.6$ (m, 4H); 2.7(s, 3H). Elemental analyses $C_8H_8N_2S_2O_2$; Calculated: C 42.07% H 3.53% $N_{-1}$12.27%; Found: C 41.97% H 3.57% N 12.14%. IR(KBr) 3100 cm$^{-1}$ 3100 cm (N-H); 1340cm$^{-1}$, 1160 cm$^{-1}$ (S=O).

EXAMPLE 2

Synthesis of N-Azetyl-2-benzothiazolesulfonamide

2-Benzothiazolesulfonamide (1.0g., 0047 mol) was dissolved in 30 ml of pyridine and stirred at room temperature for 15 minutes. Freshly distilled acetic anhydride (2 ml) was added to this solution and the reaction stirred over night at room temperature. The reaction was poured into a 300 ml beaker containing 25 ml of concentrated $HC_1$ and 250 of crushed ice. The reaction was allowed to stand at room temperature until the ice melted and then vacuum filtered to yield 0.2 g of product (quantitative yield). The product was purified by adding the crude product to 25 ml of 10% $Ha_2CO_3.H_2O$ solution, filtering the sodium salt of N-acetyl-2-benzothiazolesulfonamide and dissolving it into water followed by careful acidification and hydrochloric acid. m.p. 197°-199° C.; NMR(DMSO-D$_6$) $\delta$8.4-7.5 (m, 5H), 2.1 (2, 3H). Elemental Analyses: $C_9H_8N_2O_3S_2$. Calculated: C 42.18%, H 3.15%, N 1-0.93%. Found: C 42.27%, H 3.14%, N 10.86%.

EXAMPLE 3

Synthesis of N-Acetyl-6-ethoxy-2-benzothiazolesulfonamide

6-Ethoxy-2-benzothiazolesulfonamide (1.0 g., 0.0039 mol) was dissolved in 30 ml of pyridine and stirred at room temperature for 15 minutes. Freshly distilled acetic anhydride (2 ml) was added and the reaction mixture stirred over night. The reaction was poured into a 300 ml beaker containing 25 ml of concentrated HCl and 250 ml of crushed ice. The reaction was allowed to stand at room temperature until the ice melted and then vacccm filtered to yield 1.0 g of product (86.0% yield). The crude product was purified by adding it to 25 ml of a 10% solution of $Na_2CO_3.H_2O$, followed by filtration of the sodium salt of N-acetyl-6-ethoxy-2-benzothiazole-sulfonamide. The sodium salt was dissolved in water and precipitated with concentrated HCl. m.p. 178°-180° C.

Additional Spectral Data:
(1) IR Data: 1725 cm-1
(2) High Resolution Mass Spectrum
 a. m/e 300.0253 (M+)
 b. Analytical for mass at 300.0253: $C_{11} H_{12}N_2O_4S_2$
 c. Calculated Mass: 300.355
 d. Calculated Analytical: $C_{11}N_{12}N_2O_4S_2$
(3) NMR Data:

| a. 1.4 ppm | triplet | 3 protons |
| b. 2.1 ppm | singlet | 3 protons |
| c. 4.2 ppm | quartet | 2 protons |

-continued

| d. 7.1–8.3 ppm | multiplet | 3 proton |

(Aromatic protons)

EXAMPLE 4

Synthesis of 6-Ethoxy-N-methyl-2-benzothiazolesulfonamide.

A solution of 40% aqueous methylamine (80 ml) was placed in a 250 ml 3-necked flask, equipped with a powerful stirrer and two-addition funnels. The solution was cooled to −10° C. with an ice/methanol bath. A solution of 6-ethoxy-2-mercaptobenzothiazole (2.0 g., 0.0095 mol) in 20 ml of 5% NaOH was prepared, cooled to 10° C. and placed into one of the addition flasks. The second addition flask was charged with 40 ml of 5.25% $NaOC_1$, which was cooled to 5° C. The two solutions were added simultaneously to the aqueous methylamine over a period of one hour with the rate of addition of the 6-ethoxy-2-mercaptobenzothiazole solution slightly faster than the addition of the $NaOC_1$ solution The temperature of the reaction was maintained at −5° C.-0° C. The reaction was stirred for 15 minutes upon completing the addition and vacuum filtered to yield 6-ethoxy-2-benzothiazolesulfenamide. The 6-ethoxy-2-benzothiazolesulfenamide was immediately dissolved in 100 ml of acetone and oxidized with 50 ml of 5% $KMnO_4$. The temperature of the oxidation was kept below 30° C. The $MnO_2$ was removed by vacuum filtration and the filter cake washed with 25 ml of 5% NaOH. The 6-ethoxy-N-methyl-2-benzothiazolesulfonamide was precipitated from the solution by acidification with 5% $HC_1$ to yield 1.3g. (yield 50.3%). The product was purified by dissolving it in 10% $Na_2CO_3$ and precipitating it with 5% Hl. m.p. 129° C.-131° C.; NMR(DMSO-d$_6$) 8.4(s, 1H), 8.3–7.1cm, 3H) 4–14–3.9(q,1 2H) 2.7(s, 3H 1.5-1.2(t, 3H. IR(KBr) 3100 cm (N-H) 1345 cm$^{-1}$, 1155 cm (S=O). Elemental Analyses: $C_{10}H_{12}N_2O_3S_2$; Calculated: C 44.09% H 4.44% N 10.28%. Found: C 44.04% H 4.51% N 10.18%.

EXAMPLE 5

Synthesis of 6-Ethoxy-N-propyl-2-benzothiazolesulfonamide n-Propyl amine (30 mL) was dissolved in a solution of 50 mL of 95% ethanol and 50 mL of water. This solution was cooled to 0° C. 6-Ethoxy-2-mercaptobenzothiazole (2.0g.; 0.0095 mol) was dissolved in 25 mL of 5% KOH and added simultaneously with 5.25% $NaOC_1$ (40 mL) to the propylamine solution at 0° C. The reaction was stirred for 30 minutes upon completing the addition and the precipitate collected. This product was dissolved in 20 mL of dimethoxyethane (DME) and cooled to 0° C. m-CPBA (m-chloroperoxybenzoic acid) (5.1g.; 0.029 mol) was taken up in 15 mL of DME and added at 0° C. to the sulfenamide solution The reaction mixture was stirred for 15 hours at room temperature and the DME removed under vacuum. m-Chlorobenzoic acid was removed by stirring the reaction with 2.5% $NaHCO_3$ solution. The sulfonamide was purified by dissolving in 5% KOH, filtered, and precipitated with dilute acetic acid (1:1) to give 1.8g. (63.1% yield) of pure A10 m.p. 112°–113° C.; NMR(DMSO-d$_6$) δ8.3-8.1(d, 1H); 7.9 (d, 1H); 7.5-7.2(q, 1H); 6.0 (s, 1H); 4.5-4.0(q, 2H); 3.2-3.0(t, 2H); 1.7-1.4(m, 5H)

EXAMPLE 6

6-Hydroxy-N-Methyl-2-benzothiazolesulfonamide

A one molar solution of boron tribromide in $CH_2Cl_2$ (21 mL) was cooled to −76° C. in a dry ice/acetone bath. N-Methyl-6-ethoxy-2-benzothiazole-sulfonamide (1, og.; 0.0037 mol) was added and the reaction stirred in the dry ice bath for four hours. The reaction was removed, stirred at room temperature for 18 hours, poured into a mixture of 25 mL of crushed ice/25 mL water and stirred for 30 minutes. The crude material was collected and purified by dissolving in 10% $Na_2CO_3$, filtered, anc precipitated with dilute acetic acid (1:1) to give 0.75g (83.0% yield) of pure product, m.p. 189°-190° C.; NMR(DMSO-d ) delta 8.5–8.0(m, 3H); 7.6(d, 1H); 7.4–7.2 (q, 1H).

EXAMPLE 7

Synthesis of 6-Hydroxy-2-Benzothiazolesulfonamide

A 1 M solution of BBR in $MCH_2Cl_2$ (23 ml., 0.022 mol) was cooled to −80° C. in a dry ice/acetone bath stirred for 20 minutes. (The reaction was accomplished under a nitrogen atmosphere.) A suspension of 6-ethoxy-2-benzothiazolesulfonamide (0.5g., 0.002 mol) in 75 ml of $CH_2Cl_2$ was added slowly to the coole bath and stirred at room temperature overnight. The reaction was poured into ice water and filtered to yield 0.35 g of product (73.8% yield). The product was purified by recrystallization from methanol and water. m.p. 209° C.; NMR(DMSO-D$_6$), δ8.4 (s, 1H), 8.3–7.0 (m, 3H), 3.5 (s, 2H); DMSO-D$_6$/D$_2$O)$^6$δ8.3-7.0 (m, 3H), 4.2 (s, 2H).

Additional Spectral Data: High Resolution Mass Spectrum a. m/e 22.99820 (M+)
b. analytical for mass at 229.9820: $C_7H_6N_2O_3S_2$
c. calculated mass: 230.264
d. Calculated analytical: $C_7H_6N_2O_3S_2$

EXAMPLE 8

Synthesis of 6-Chloro-2-benzothiazolesulfonamide

4-Chloroaniline (14.3g, .112mol) was dissolved in 30 mL of glacial acetic acid and added slowly to $S_2Cl_2$ (75 mL) cooled in a $CH_2OH$—ice bath. The reaction was stirred for 15 hours at room temperature. It was then increased to 50° C. for 4 hours and then to 78° C. for 3 hours. The reaction was cooled and 100 mL of dry benzene added. The mixture was stirred for 30 minutes and filtered. The product was washed two times with 25 mL of benzene. The green/yellow substance was added to 250 mL of crushed ice and 150mL of $H_2O$ and stirred 3 hours. The purple product was filtered and added with vigorou stirring to cooled 5% NaOH. The reaction was stirred to one hour, filtered and the pH adjusted to 7 with dilute acetic acid. The product precipitated and was isolated by vacuum filtration to yield 10.7g of 5-chloro-2-aminobenzenethiol (59.8% yield): m.p. 70°–72° C.; NMR(DMSO-d$_6$) δ7.3–6.7(m, 3H); 5.7-4.7(s, 3H); mass spectrum, m/e 159(M calcd. 159.6) 5-Chloro-2-aminobenzenethiol(15g, 0.095mol) was dissolved in 5% NaOH and 17mL of carbon disulfide were added. The reaction was stirred 15 hours at room temperature and heated at reflux for 3 hours. The pH of the reaction was adjusted to 6 with dilute acetic acid and filtered to yield 16.9g of 6-chloro-2-mercaptobenzothiazole (89.4% yield): m.p. 243°-246° C. (decomposes); NMR(DMSO-d$_6$) δ11.5(s, 1H); 8.0-7.2(m, 3H)

EXAMPLE 9

Synthesis of 6-0-Acetyl-N-Acetyl-2-benzothiazolesulfonamide

6-Hydroxy-2-benzothiazolesulfonamide (1.0 g., 0.004 mol) was dissolved in 30 ml of pyridine Acetic anhydride (4 ml) was added and the reaction was stirred at room temperature for 18 hours. The reaction mixture was poured into 40 ml of conc. HC and 300 ml of crushed ice. The solid which precipitated was collected and dried to afford 0.65 g of product. (yield) m.p. 155°-157° C. NMR (DMSO-D$_6$); δ2.1 ppm. singlet; δ2.4 ppm, singlet. (The N-acetyl is at 2.1 ppm and the 0-acetyl at 2.4 ppm.) The TLC shows the product to be pure.

EXAMPLE 10

Rabbit Eye Tests (In-Vivo IOP Determinations)

New Zealand albino rabbits either sex and weighing 1.9-2.4kg were used. Control IOP measurements were made by applanation tonometry (Alcon Applanation Pneumatonograph ®) prior to water loading and drug administration. The rabbits were first anesthelized and then water loaded using 100 ml/kg (sterile water for injection). The water dose was given intraperitoneally over 15-20 minutes Four test formulations were administered topically to the right eye of each rabbit immediately following water loading. The vehicle was administered to the left eye of each rabbit. The test formulations contained 1% suspensions of ethoxzolamide, and the other indicated compounds, and a vehicle (coded E). The vehicle contained a pH 7.2 phosphate buffer and 0.05% polysorbate 80 (Tween-80 ®). IOP measurement were made in right and left eyes at 15, 30, 30, 60, 90, 120 and 180 minutes after topical administration.

EXAMPLE 11

SALTED RABBIT TEST

For reasons that are not quite fully understood, it has been found that if the rabbits prior to exsanguanation are treated with a salt diet, the test results are more reproducible and accurate In particular, an initial drop followed by two drops at one minute intervals are applied to one eye of each of 15 adult white rabbits that had been maintained on a diet containing 0.5% sodium. The treated eye was selected randomly, whereas, the fellow eye received placebo; the observer was masked. Results identified a small but significant reduction of intraocular pressure in the treated eye at 30, 60 and 120 minutes In particular, a 1% w/v suspension of 6-chloro-2-benzothiazolesulfonamide analog was prepared in a standard vehicle consisting of aqueous pH 7.8 phosphate buffer, 0.05% w/v tween 80, and sufficient NaC$_1$ to make the preparation isotonic. One drop, followed by two drops each at one minute intervals, was applied to one eye of normal adult white rabbits. Fifteen rabbits were used in the experiment. The treated eye was selected randomly, whereas, the fellow eye received placebo. The observer was masked. The intraocular pressure (IOP) was measured with an Alcon implantation pneumotonometer. A drop of local anesthetic was applied just prior to making the measurement. The IOP was measured in both rabbit eyes at 0, 30, 60, 90 and 120 minutes following instillation of the new antiglaucoma agent. The results are shown as follows:

| | IOP* CHANGES 30 THROUGH 120 MINUTES Time of Measurement (Minutes) | | | | |
|---|---|---|---|---|---|
| Rabbit No. | 0** | 30 | 60 | 90 | 120 |
| 1 | +1 | -3 | -2 | -1 | -2 |
| 2 | +2 | -5 | -4 | -2 | -4 |
| 3 | 0 | +1 | +1 | +1 | +3 |
| 4 | 0 | 0 | -2 | -3 | -1 |

| | EXAMPLE 10 TABLE - Water Loading Model** | | | | | | | |
|---|---|---|---|---|---|---|---|---|
| Time | No Drug | | Ethoxzolamide | | 6-Ethoxy-N-methyl benzothiazole-2-sulfonamide | | 6-Chloro benzothiazole-2-sulfonamide | |
| (Min) | R | L | R | L | R | L | R | L |
| 0 | 12.96* | 13.19 | 14.94 | 14.53 | 14.10 | 14.10 | 14.33 | 14.50 |
| | (1.26) | (1.18) | (1.76) | (1.90) | (2.0) | (1.3) | (0.77) | (1.86) |
| 15 | 20.41 | 18.48 | 21.07 | 20.33 | 19.10 | 19.62 | 19.72 | 19.17 |
| | (1.62) | (3.08) | (4.54) | (5.23) | (3.45) | (2.96) | (2.42) | (3.94) |
| 30 | 22.04 | 21.54 | 21.60 | 22.40 | 19.90 | 20.14 | 20.00 | 20.78 |
| | (1.7) | (1.28) | (2.85) | (2.90) | (3.71) | (3.12) | (2.43) | (2.69) |
| 60 | 21.85 | 21.74 | 21.33 | 21.08 | 20.33 | 20.20 | 21.39 | 20.67 |
| | (2.07) | (1.72) | (1.67) | (1.68) | (4.08) | (2.80) | (2.52) | (1.68) |
| 90 | 20.07 | 20.37 | 20.33 | 20.40 | 18.57 | 20.67 | 19.11 | 18.89 |
| | (2.38) | 1.42 | (2.74) | (2.26) | (2.25) | (1.93) | (1.94) | (2.61) |
| 120 | 17.81 | 18.56 | 18.80 | 19.13 | 17.24 | 18.62 | 18.78 | ⁏.00 |
| | (2.99) | (1.74) | (2.34) | (0.92) | (3.21) | (2.38) | (1.86) | (2.03) |
| 180 | 17.3 | 16.63 | 16.4 | 16.07 | 17.00 | 17.29 | 17.8 | 16.53 |
| | (2.89) | (1.94) | (1.59) | (2.40) | (1.92) | (2.59) | (1.61) | (1.64) |
| η = *** | 9 | | 5 | | 7 | | 6 | |

The compound 6-ethoxy-N-methyl-2-benzothiazole shows a significant drop in IOP (right eye) compared to the no-drug control at 90 and 120 minutes. The compound 6-chloro-2-benzothiazole shows a significant drop from 15 through 90 minutes. As demonstrated in Example 10, ethoxzolamide showed no effect at any time point when compared to the no drug control. It is surprising, as shown by the tests of this example, that ethoxzolamide shows no effect and yet 6-chlorobenzothiazole-2-sulfonamide proved effective.

*mmHg pressure measurement
**Drug was administered topically (50 ul q 2 min × 6) to the right eye; vehicle was administered to the left eye.
***η = number of rabbits tested.

-continued

| IOP* CHANGES 30 THROUGH 120 MINUTES Time of Measurement (Minutes) | | | | | |
|---|---|---|---|---|---|
| 5 | +3 | −4 | −3 | −3 | −5 |
| 6 | +1 | −1 | −2 | −3 | −1 |
| 7 | 0 | 0 | −2 | −2 | 0 |
| 8 | +2 | −2 | −4 | −2 | −6 |
| 9 | −2 | 0 | +2 | +2 | 0 |
| 10 | −1 | −1 | −2 | 0 | 0 |
| 11 | −1 | 0 | −1 | 0 | −2 |
| 12 | +1 | 0 | −3 | −3 | −5 |
| 13 | 0 | 0 | +2 | +2 | +1 |
| 14 | −3 | +2 | +3 | +3 | +3 |
| 15 | +1 | −1 | −2 | −2 | −2 |
| Average Change = | +0.27 | −0.93 | −1.27 | −0.87 | −1.47 |
| ± Std. Dev.= | 1.58 | 1.87 | 2.22 | 2.07 | 2.64 |
| Paired t value = | — | −1.834 | −2.106 | −1.63 | −2.11 |
| Probability (1.t.) = | — | 0.05 | 0.025 | 0.1 | 0.025 |

| | | |
|---|---|---|
| IOP* Changes | = | $(IOP_{DET} - IOP_{CET}) - (IOP_{DEO} - IOP_{CEO})$ where |
| $IOP_{DET}$ | = | IOP measurement (mm Hg) of dosed eye at time t. |
| $IOP_{DEO}$ | = | IOP measurement (mm Hg) of dosed eye at t = 0, but prior to receiving dose. |
| $IOP_{CET}$ | = | IOP measurement (mm Hg) of control (non-dosed) eye at time t. |
| $IOP_{CEO}$ | = | IOP measurement (mm Hg) of control eye at time t = 0 |

**Difference in IOP measurements (mm Hg) between both eyes just prior to dosing at t = 0 (i.e., $IOP_{DEO} - IOP_{CEO}$).

The lowering of IOP was statistically significant at 30, 60, and 120 minutes dosing. This is shown in the data columns at 30, 60, 90 and 120 minutes by the negative average change in IOP as compared to the zero time value (+0.27).

EXAMPLE 12

Example 10 shows a comparison of compositions of this invention with ethoxzolamide in a water loading model. In this example we show testing of rabbits fed on a sodium enriched diet (Salted Rabbit Test) for ethoxzolamide to allow comparison with the invention data of Example 11.

Using the same procedure as described in Example 11, the parent drug ethoxzolamide was tested for significant lowering of IOP.

| IOP* Changes 30 Through 120 Minutes Time of Measurement (Minutes) | | | | | |
|---|---|---|---|---|---|
| Rabbit No. | 0** | 30 | 60 | 90 | 120 |
| 1 | +4 | +1 | +3 | +1 | 0 |
| 2 | +1 | +2 | −2 | 0 | −1 |
| 3 | −1 | −2 | +2 | +2 | +2 |
| 4 | 0 | +1 | +1 | −2 | −1 |
| 5 | −1 | −3 | −2 | −3 | −1 |
| 6 | +1 | 0 | 0 | +2 | +2 |
| Average change = | +.67 | −.17 | +.33 | −0 | +.17 |
| Stnd. Dev. = | — | 1.60 | 2.07 | 2.25 | 2.43 |
| Paired, t value = | — | 1.27 | 0.40 | 0.73 | 0.50 |
| Statistical sign = | — | N.S. | N.S. | N.S. | N.S. |

No lowering of IOP could be detected at any time point after dosing (N.S. = non-significant).

*See example 10.
**See Example 10.

In a comparison of ethoxzolamide and 6-chloro-2-benzothiazole-sulfonamide in the two well recognized rabbit models of Examples 10 and 11, ethoxzolamide showed no effectiveness, whereas the 6-chloro-2-benzothiazole was pharmacologically active (lowered IOP).

What is claimed is:

1. A topical composition for eye drop treatment of glaucoma, comprising a small but therapeutically effective intraocular eye pressure reducing amount of a benzothiazole-2-sulfonamide, carbonic anhydrase inhibitor of the formula:

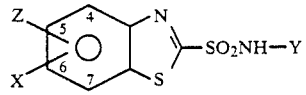

wherein both X and Z are selected from the group consisting of hydrogen, halogens, methoxy $C_1$ to $C_6$ alkoxy, amino, amide, nitro, and trifluoromethylsulfonyl, and wherein if either "X" or "Z" is hydrogen, the other is not hydrogen; and Y is selected from the group of hydrogen and $C_1$ to $C_6$ alkyl; and an inert, non-eye irritating, non-toxic eye drop diluent.

2. The composition of claim 1 wherein said sulfonamide is at a concentration of from about 0.25% to about 5% by weight of said eye drop treating composition.

3. The composition of claim 2 wherein said sulfonamide is from about 0.5% to about 2.0% by weight of said eye drop treating composition.

4. The composition of claim 3 wherein said sulfonamide is about 1% by weight of said eye drop treating composition.

5. The composition of claim 1 wherein said diluent is an isotonic eye treatment carrier, diluent formulation buffered to a pH of from about 4.0 to about 8.0, and containing small but effective amounts of a wetting agent and an anti-bacterial agent.

6. The composition of claim 1 wherein said diluent is an isotonic eye treatment carier, diluent formulation buffered to a pH of from about 6.8 to about 7.8, and containing small but pharmaceutically effective amounts of a wetting agent and an anti-bacterial agent.

7. The composition of claim 5 wherein said wetting agent is Tween 80.

8. The composition of claim 5 wherein said anti-bacterial agent is benzalkonium chloride.

9. The composition of claim 8 wherein the amount of said anti-bacterial is from 0.004% to 0.02% by weight of said eye drop treatment composition.

10. The composition of claim 1 wherein Z and Y are hydrogen and X is a 6 position substituent.

11. The composition of claim 10 wherein X is a halogen.

12. The composition of claim 10 wherein X is chloro, fluoro, or bromo.

13. The composition of claim 12 wherein X is chloro.

14. A topical composition for eye drop treatment of glaucoma, comprising a small but therapeutically effective intraocular eye pressure reducing amount of a benzothiazole-2-sulfonamide, carbonic anhydrase inhibitor of the formula:

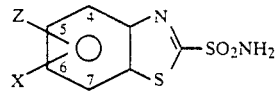

wherein both X and Z are selected from the group consisting of hydrogen and halogens, but wherein both X and Z are not hydrogen at the same time; and an inert, non-eye irritating, non-toxic eye drop diluent.

15. A method of topically treating glaucoma with eye drops to reduce intraocular pressure, comprising tropically applying to the eye a small but therapeutically effective intraocular eye pressure reducing amount of a benzothiazole-2-sulfonamide of the formula:

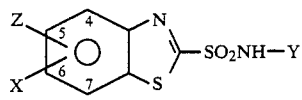

wherein both X and Z are selected from the group consisting of hydrogen, halogen, methoxy, $C_1$ to $C_6$ hydroxy-alkoxy, amino, amide, nitro, and trifluoromethylsulfonyl, and wherein if either X or Z is hydrogen, the other is not hydrogen; and Y is selected from the group consisting of hydrogen and $C_1$ to $C_6$ alkyl; in an inert, non-eye irritating, non-toxic eye drop diluent.

16. The method of claim 1 wherein said sulfonamide is present at a concentration of from about 0.25% to about 5.0% byh weight of said sulfonamide and diluent combination.

17. The method of claim 16 wherein the dosage for topical application is three drops, with one drop every two minutes.

* * * * *